(12) United States Patent
Barnikol (10) Patent No.: US 7,598,220 B2
(45) Date of Patent: *Oct. 6, 2009

(54) USE OF HYPERPOLYMERIC HEMOGLOBIN FOR THE TREATMENT OF PULMONARY EDEMA

(75) Inventor: Wolfgang Barnikol, Mainz (DE)

(73) Assignee: SanguiBio Tech GmbH, Witten (DE)

( * ) Notice: Subject to any disclaimer, the term of this patent is extended or adjusted under 35 U.S.C. 154(b) by 298 days.

This patent is subject to a terminal disclaimer.

(21) Appl. No.: 10/578,428

(22) PCT Filed: Nov. 2, 2004

(86) PCT No.: PCT/EP2004/012363

§ 371 (c)(1),
(2), (4) Date: May 5, 2006

(87) PCT Pub. No.: WO2005/046717

PCT Pub. Date: May 26, 2005

(65) Prior Publication Data

US 2007/0049517 A1 Mar. 1, 2007

(30) Foreign Application Priority Data

Nov. 12, 2003 (DE) ................... 103 52 692

(51) Int. Cl.
*A61K 38/40* (2006.01)
*A61K 38/41* (2006.01)
*A61K 38/42* (2006.01)

(52) U.S. Cl. .......................................... 514/6; 424/445

(58) Field of Classification Search ........................ None
See application file for complete search history.

(56) References Cited

U.S. PATENT DOCUMENTS

| | | | | |
|---|---|---|---|---|
| 5,234,903 | A * | 8/1993 | Nho et al. ......................... | 514/6 |
| 5,665,383 | A * | 9/1997 | Grinstaff et al. ............. | 424/450 |
| 5,985,332 | A | 11/1999 | Barnikol et al. | |
| 6,432,918 | B1 * | 8/2002 | Winslow ......................... | 514/6 |
| 2004/0022839 | A1 | 2/2004 | Barnikol | |
| 2004/0242846 | A1 | 12/2004 | Barnikol | |

FOREIGN PATENT DOCUMENTS

| | | |
|---|---|---|
| DE | 197 01 37 | 10/1967 |
| DE | 37 14 351 | 11/1988 |
| DE | 35 76 651 | 4/1990 |
| DE | 38 41 105 | 6/1990 |
| DE | 44 18 937 | 8/1995 |
| DE | 44 18 973 | 12/1995 |
| DE | 197 01 037 | 7/1998 |
| DE | 100 31 742 | 1/2002 |
| DE | 100 31 744 A1 | 1/2002 |
| DE | 100 31 740 A1 | 2/2002 |
| EP | 97 100 790 | 1/1983 |
| WO | WO 02/00230 A | 1/2002 |
| WO | WO 02/00768 A | 1/2002 |
| WO | WO 03/094953 A | 11/2003 |

OTHER PUBLICATIONS

Riess, J.G.: "Oxygen Carriers (Blood Substitutes)—Raison d'Etre, Chemistry, and some Physiology," Chemical Reviews 101 (2001): 2797-2919. (pp. 2797-2800 enclosed).
Böcker, W., Denk, H., Heitz Ph. U (Ed.): Pathology, Urban & Schwarzenberg, Munich and elsewhere 1997; (Spec. p. 6) (Front Page and List of Contents Enclosed).
Gerok W., Huber C., Meinertz T., Zeidler, H. (Ed.): Gross-Schölmerich-Gerock-Die Innere Medizin, $10^{th}$ completely new revision and expanded edition, Schattauer, Stuttgart and New York 2000. (Spec. pp. 6-7). (Front page and List of contents Enclosed).
Weihrauch, T.R. (Ed.): Wolff-Weihrauch-Internistische Therapie 2000/2001, $13^{th}$ revised edition, Urban & Fisher, Munich, and Jena 2000 (Spec. p. 7) (Front page and List of contents Enclosed).
Vazquez, R.M., "Nursing care for the patient . . . ," Arch. Cardio. Mex., vol. 72, pp. 280-285 (Spec. p. 7) (English Abstract).
Katren V.: "The Conjugation of Proteins with Polyethylene Glycol and Other Polymers—Altering Properties of Proteins to Enhance Their Therapeutic Potential," Advanced Drug Delivery Reviews 10 (1993): 91-114) (Spec. p. 9).
Vandegriff KD: "Haemoglobin-Based Oxygen Carriers" Expert Opinion on Investigational Drugs, Ashley Publications Ltd., London, GB, vol. 9, No. 9, 2000, pp. 1967-1984, XP008034792, ISSN: 1354-3784.
Barnikol et al: "Hyperpolymere Hämoglobine als künstliche Sauerstoffträger" Therapiewoche, vol. 15, 1996, pp. 811-815, XP09044173.
Barnikol Wolfgang K R et al: "New artificial oxygen carriers made of pegulated polymerised pyridoxylated porcine haemoglobin (P4Hb)" Comparative Biochemistry and Physiology Part A Molecular and Integrative Physiology, vol. 132A, No. 1, May 2002, pp. 185-191, XP002318526 ISSN: 1095-6433.
Vandegriff KD: "Haemoglobin-Based Oxygen Carriers" Expert Opinion on Investigational Drugs, Ashley Publications Ltd., London, GB, vol. 9, No. 9, 2000, pp. 1967-1984, XP008034792, ISSN: 1354-3784.

(Continued)

Primary Examiner—Lisa J Hobbs
(74) Attorney, Agent, or Firm—Collard & Roe, P.C.

(57) ABSTRACT

This invention relates to the use of hypo-oncotic aqueous solutions of molecularly dispersed chemically modified high molecular weight crosslinked hemoglobins, namely so-called hemoglobin hyperpolymers, to prepare agents for the symptomatic, primarily life-saving treatment of acute pulmonary edema. Administration in particular is intravascular. Surprisingly, additive administration can be performed since according to the invention the colloidal-osmotic (=oncotic) pressure of the blood itself is essentially raised only slightly, and the blood volume is increased hardly at all. Administration pursuant to the invention is thus (almost) volume-neutral based on the blood into which the injection is made. A hyperpolymeric hemoglobin derivative is thus used therapeutically for the first time as a blood additive for the treatment of pulmonary edema.

7 Claims, 2 Drawing Sheets

OTHER PUBLICATIONS

Barnikol WK R et al: "Haemoglobin hyperpolymers, a new type of artificial oxygen carrier—Concept and current state of development" Transfusion Medicine and Hemotherapy, vol. 31, No. 4, Aug. 2004, pp. 269-281, XP 009044191 ISSN: 1660-3796.

Riess, J.G.: "Oxygen Carriers (Blood Substitutes)—Raison d'Etre, Chemistry, and some Physiology," Chemical Reviews 101 (2001): 2797-2919. (Spec p. 2) to follow.

Böcker, W., Denk, H., Heitz Ph. U (Ed.): Pathology, Urban & Schwarzenberg, Munich and elsewhere 1997; (Spec. p. 6) to follow.

Gerock W., Hube CH, Meinertz T., Zeidler, H. (Ed.): Gross-Schölmerich-Gerock-Die Innere Medizin, 10$^{th}$ completely new revision and expanded edition, Schattauer, Stuttgart and New York 2000. (Spec. pp. 6-7). to follow.

Weikrauch, T.R. (Ed.): Wolff-Weikrauch-Internistische Therapie 2000/2001, 13$^{th}$ revised edition, Urban & Fisher, Munich, and Jena 2000 (Spec. p. 7) to follow.

Arch. Cardio. Mex., vol. 72, pp. 280-285 (Spec. p. 7) to follow.

Katren, V.: "The Conjugation of Proteins with Polyethylene Glycol and Other Polymers—Altering Properties of Proteins to Enhance Their Therapeutic Potential," Advanced Drug Delivery Reviews 10 (1993): 91-114) (Spec. p. 9) to follow.

Pötzschke H. et al. (1997): "Molar Masses and Structure in Solution of Haemoglobin Hyperpolymers—A Common Calibration of Size Exclusion Chromatography of These Artificial Oxygen Carriers," Artificial Cells, Blood Substitutes, and Immobilization Biotechnology 25, 527-540) on Sephacryl S-400 HR gel (Pharmacia Biotech, Freiburg, Germany) (Spec. p. 24) to follow.

* cited by examiner

USE OF HYPERPOLYMERIC HEMOGLOBIN FOR THE TREATMENT OF PULMONARY EDEMA

CROSS REFERENCE TO RELATED APPLICATIONS

Applicant claims priority under 35 U.S.C. §119 of German Application No. 103 52 692.7 filed Nov. 12, 2003. Applicant also claims priority under 35 U.S.C. §365 of PCT/EP2004/012363 filed Nov. 2, 2004. The international application under PCT article 21(2) was not published in English.

OBJECT OF THIS INVENTION

This invention relates to the use of hypo-oncotic aqueous solutions of molecularly dispersed chemically modified high molecular weight crosslinked hemoglobin, so-called hemoglobin hyperpolymers, for producing agents for the symptomatic, primarily life-saving treatment of acute pulmonary edema. Their administration is intravascular in particular. Surprisingly, additive administration can be performed, since pursuant to the invention the colloidal-osmotic (=oncotic) pressure of the blood is raised only slightly and the blood volume is therefore hardly increased at all. The use and administration according to the invention is thus (almost) volume-neutral based on the blood into which injection is performed. A hyperpolymeric hemoglobin derivative is thus used therapeutically for the first time as a blood additive for the treatment of pulmonary edema.

BACKGROUND OF THE INVENTION

1. Artificial Oxygen Carriers

Artificial oxygen carriers/transporters are an extremely heterogeneous group of substances. Their name-giving characteristics are their ability to bind oxygen in the form of molecular dioxygen ($O_2$) reversibly or to dissolve it—thus in principle they have a property in common with the natural oxygen carrier/transporter in the blood, hemoglobin (red blood pigment) that occurs in the erythrocytes (red blood cells)—and their potential usefulness as pharmaceuticals to be administered intravascularly (usually intravenously), or in other biomedical applications.

(A comprehensive review (state of the art) in: RIESS J. G.: "Oxygen Carriers ("Blood Substitutes)—Raison d'Etre, Chemistry, and some Physiology," Chemical Reviews 101 (2001): 2797-2919; a review of many hemoglobin derivatives in: VANDEGRIFF K. D.: "Haemoglobin-based Oxygen Carriers": Expert Opinions on Investigational Drugs 9 (2000): 1967-1984).

The known oxygen carriers differ both with respect to their nature and with respect to the resultant physicochemical properties and their usability.

Thus, perfluorocarbons are immiscible with and insoluble in aqueous solutions, such as blood plasma for example. However, they can be emulsified therein in the form of finely dispersed droplets (stabilized with emulsifiers). Liposomes filled with natural or artificial oxygen carriers are likewise emulsified or suspended. These are vesicles (artificial cells or artificial erythrocytes) surrounded by a phospholipid double layer membrane.

Hemoglobins, their derivatives obtainable by chemical modification, and isolated and necessarily chemically modified heme groups can be dissolved freely in the aqueous phase (in plasma, for example).

The molecular structure of artificial oxygen carriers determines their method of administration, especially whether they can be substituted as a replacement for missing blood, or whether they can be added to existing blood as an additive. Products described up to now are intended to be oxygen-transporting plasma substitutes, or a plasma replacement fluid to fill up the vascular system partially drained by acute hemorrhage or by blood withdrawal, which in contrast to the known (non-oxygen-transporting) plasma substitutes also restore another essential function of the blood, namely oxygen transport.

Perfluorocarbons and liposomes do not dissolve in aqueous blood plasma; as a distinctly separate emulsified or suspended phase of their own, they have and they occupy a certain volume, and therefore they seem suitable in principle for the mentioned purpose as oxygen-transporting plasma substitutes, but on the other hand not as additives to the blood since they necessarily increase its volume.

To be suitable as a replacement for missing blood, oxygen-transporting plasma substitutes of hemoglobins or of their derivatives obtained by chemical modifications freely dissolved in an aqueous phase have to be both isotonic (tonicity is a relative measure of osmotic pressure) and isoncotic (=iso-oncotic; oncoticity is a measure of the oncotic (=colloidal-osmotic) pressure) with the blood plasma. To produce isotonicity, such artificial oxygen carriers are usually dissolved in an electrolyte solution that resembles blood plasma electrolytes.

Hemoglobin derivatives developed (and published) up to now as artificial oxygen carriers themselves involve iso-oncoticity in pharmaceutical preparations. Their molecular design conforms to the clinical requirement for iso-oncoticity, which is accomplished by a sufficient number of oncotically active drug molecules.

For this reason, such freely dissolved hemoglobin derivatives are also very particularly proposed for use in case of (severe) blood loss. They are only very conditionally usable (namely extremely limited in amount/dose) for medical indications without blood loss, since because of their mentioned properties, they necessarily increase blood volume by the volume of their injected or infused pharmaceutical preparation.

2. Hemoglobin Hyperpolymers

If artificial oxygen carriers are to be used as additives to treat oxygen deficiency, they should have a sufficiently low colloidal-osmotic pressure (cf. Barnikol W. K. R. et al. (1996): "Hyperpolymeric hemoglobins as artificial oxygen carriers—an innovative approach to medical development," Therapiewoche 46: 811-815). They are planned as artificial oxygen carriers to increase the oxygen transport capacity of existing blood when no blood loss is to be replaced. For hemoglobin hyperpolymers after injection or infusion not permanently to increase the volume of circulating blood (but instead for the water and the salts of their preparation to be extensively excreted again through the kidneys), the oncotically active number of drug molecules has to be reduced as much as possible. To this end, the hemoglobins are crosslinked and polymerized chemically (by means of polyfunctional or bifunctional crosslinking agents). Giant artificial oxygen-binding molecules are formed in this way. From the chemical viewpoint, molecularly crosslinked hemoglobins are multimers of the monomer. However, this says nothing about what multimers—and this involves a broad distribution of molecular weights with oligomers and higher polymers—have what effects on the properties of the overall product.

3. Pulmonary Edema

Edema is an abnormal fluid accumulation in the intercellular space (interstitium). Pulmonary edemas are a frequent clinical syndrome. They lead to a life-threatening impairment of health that leads to death in severe cases. Distinction is made principally between cardiac (obstructive) edema caused by insufficiency of the left ventricle and pulmonary edema of toxic genesis from elevated capillary permeability with pulmonary inflammation, inhalation of injurious gases, for example, also from high oxygen concentrations, uremia, or hypersensitivity reactions, etc.

Therapy is always symptomatic with regard to the life-threatening impairment of pulmonary function (intensive medical care, corticoids to suppress inflammatory processes, oxygen-enriched respiratory air, and pressurized respiration, etc.), and if possible causal with regard to the causes (exposure prophylaxis, therapy for cardiac insufficiency, or for the underlying kidney disease, etc.).

(For the state of the art, for example, see: Böcker, W., Denk, H., Heitz Ph. U (Ed.): Pathology, Urban & Schwarzenberg, Munich and elsewhere 1997; Gerock W., Huber C H, Meinertz T., Zeidler, H. (Ed.): Gross•Schölmerich•Gerock—Die Innere Medizin, 10th completely new revision and expanded edition, Schattauer, Stuttgart and New York 2000; Weikrauch, T. R. (Ed.): Wolff—Weikrauch—Internistische Therapie 2000/2001, 13th revised edition, Urban & Fischer, Munich, and Jena 2000; Arch. Cardio. Mex., Vol. 72, pages 280-285).

PURPOSE OF THE INVENTION

The task underlying this invention is to make available improved symptomatic therapy of acute pulmonary edema, particularly of the high lethality of these diseases (mortality is said to be between 30 and 90% clinically).

Solution of the Task

This task is accomplished pursuant to the invention by producing and using a hypo-oncotic solution of chemically modified high molecular weight crosslinked hyperpolymeric hemoglobins. Surprisingly, acute pulmonary edema can be treated and mortality reduced with such solutions.

DETAILED DESCRIPTION OF THE INVENTION

According to this invention, acute pulmonary edema can be treated effectively by administering an aqueous solution of hyperpolymeric hemoglobin derivatives that can be added to the blood, whose oncotic pressure in aqueous solution is much lower than that of the existing blood and thus shows a hypo-oncotic pressure as an additive.

PARTICULAR EMBODIMENTS OF THE INVENTION

Agents are made available and used according to the invention, namely aqueous solutions containing the mentioned hyperpolymeric hemoglobins. In particular, the aqueous solutions are solutions containing electrolytes. Above all, they correspond to the physiological medium. The chemically modified oxygen carriers (hyperpolymeric hemoglobins) used pursuant to the invention originate from humans, pigs, or cattle. They preferably originate from pigs.

The hyperpolymeric hemoglobins used pursuant to the invention are high molecular weight, intermolecularly crosslinked hemoglobins. The intermolecular crosslinking of hemoglobins is generally known and is described, for example, in DE 197 01 037, EP 97 100790, DE 44 18 973, DE 38 41 105, DE 37 14 351, DE 35 76 651. These known methods are therefore incorporated here.

The hemoglobin hyperpolymers can be further modified chemically in many ways other than intermolecular crosslinking (polymerization). For example, chemically reactive effectors can be covalently linked to modify the affinity and cooperativeness of ligand binding. Other macromolecules (for example, such as polyethylene oxides, polyethylene glycols, dextrans, hydroxyethylstarches, etc.) with different chain lengths (molecular weights) can be covalently linked for various desired functional improvements of the hemoglobin hyperpolymers, for example to reduce their immunogenicity or to lengthen residence time in the vascular system (Katren, V.: "The Conjugation of Proteins With Polyethylene Glycol and Other Polymers—Altering Properties of Proteins to Enhance Their Therapeutic Potential," Advanced Drug Delivery Reviews 10 (1993): 91-114), or to improve compatibility with proteins of the 'recipient' blood plasma (DE 100 31 744 A 1).

In a preferred embodiment, a macromolecule, especially a polyalkylene oxide, is covalently bonded to the modified hyperpolymeric hemoglobin.

An especially preferred embodiment of the invention uses hemoglobin hyperpolymers that are prepared according to the German Patent Applications DE (OS) 100 31 740, DE (OS) 100 31 742, and DE (OS) 100 31 744 A1 whose contents are incorporated here. They are polymerized products (intermolecular crosslinking), with pegylation (covalent linking with polyalkylene oxides) also having been carried out.

In another preferred embodiment, still another additional reaction can be carried out if desired with chemically reactive effectors such as pyridoxal 5'-phosphate or 2-nor-2-formylpyridoxal 5'-phosphate (intramolecular crosslinking), or the reaction can also occur in the presence of chemically unreactive effectors of oxygen binding such as 2,3-bisphosphoglycerate, inositol hexaphosphate, inositol hexasulfate, or mellitic acid, or a combination of this reaction and medium conditioning can be performed. Such products are known and are described as stated above.

Preferred are oxygen carriers that are polymerized, for example with the bifunctional crosslinkers known for intermolecular reaction, such as butadiene diepoxide, divinyl sulfone, diisocyanate, especially hexamethylenediisocyanate, cyclohexanediisocyanate, and 2,6-bisisocyanatobenzensulfonic acid, di-N-hydroxysuccinimidyl ester, diimidoester or dialdehyde, particularly glyoxal, the similarly reactive glycolaldehyde, or glutaraldehyde. These products are then linked in particular with a polyethylene glycol or with other suitable macromolecules. Among them, for example, are polyethylene oxide, polypropylene oxide, or a copolymer of ethylene oxide and propylene oxide, or an ester, ether, or esteramide thereof. It is also preferred for the covalently linked polyalkylene oxide to have a molecular weight of 200 to 5000 g/mole.

The preparation of such modified oxygen binders is described in the aforementioned German Patent Applications and is incorporated herein.

Very highly preferred are hyperpolymers that are prepared from deoxygenated swine hemoglobin with glutaraldehyde as the bifunctional crosslinker and polyethylene glycol as the covalently bonded macromolecule for surface modification; see DE 100 31 740 A1 or DE 100 31 744 A1. It has been found according to the invention that hemoglobin hyperpolymers with an (average) degree of polymerization that is large enough for it to be able to be introduced into the blood as an artificial oxygen carrier as a therapeutic blood additive (without increasing the blood volume more than slightly, see above) are suitable if they produce only a certain low oncotic pressure in an aqueous electrolyte solution. This is related to the suitable average degree of polymerization (or to the proportional molecular weight) of the modified polymeric hemoglobin. This involves the number average, because the number of effective molecules is responsible for the oncotic pressure.

It has been found in particular that the mentioned hyperpolymers are suitable when their degree of polymerization is high enough for the oncotic pressure of solutions to be below 5 mbar with the therapeutic concentrations of the chemically modified high molecular weight crosslinked hemoglobins in an aqueous medium containing electrolyte (with no other macromolecules). This is about ⅐ (less than 15%) of the oncotic pressure of human blood plasma, which is about 35 mbar (administration of amounts of hemoglobin hyperpolymers that produce the mentioned therapeutic concentrations in blood plasma therefore lead to increases of blood plasma volume of no more than about 15%).

For ideal solutions, the oncotic pressure ($\pi_{onc}$) can be calculated according to the following equation from the molar weight (M) and the content (as the measured concentration $c_m$) of the dissolved colloid, and the universal gas constant (R) and the absolute temperature (T):

$$\pi_{onc} = c_m \cdot R \cdot T \cdot M^{-1}$$

For an upper limit of oncotic pressure ($\pi_{onc}$) of 5 mbar established as described for a blood additive, a minimum molecular weight (as a number average) of the hemoglobin hyperpolymer of M=(4,910 L/mole)·$c_m$ is calculated according to this formula from a desired therapeutic concentration ($c_m$) in the blood plasma, and for 2 mbar it is M=(12,300 L/mole)·$c_m$.

Real solutions, however, show instead a deviation of oncotic pressure to larger values increasing with the concentration of the colloid. The formula given for ideal solutions in the best case, therefore, can be used to estimate minimum molecular weights, while the real oncotic pressure has to be determined experimentally for real existing polymers, especially since it does not depend in a predictable way on the structural makeup of the polymers. For example, for Batch MR A-A used in the examples, from a concentration of 20 g/L, and an oncotic pressure of about 1 mbar, an associated (ideal) molecular weight of 491,000 g/mole is calculated (the following values are taken from the experimentally determined curve of oncotic pressure versus the weight concentration, shown as FIG. 1), while the experimentally determined actual molecular weight was only 320,000 g/mole.

Very especially preferred are modified hemoglobins of the type described whose aqueous electrolyte solutions show an oncotic pressure of less than 2 mbar.

All solutions with compositions of salts that imitate or resemble the human extracellular medium (including the physiological pH, usually about 7.4 (between 7.1 and 7.6)), particularly including all complete electrolyte infusion solutions for electrolyte infeed and circulatory support (review in Red List Service GmbH (Ed.): Red List 2002—List of drugs for Germany (including EU licenses and certain medicinal products), ECV, Aulendorf 2002 (Chapter 52, "52. Infusion and Standard Injection Solutions, Organ Perfusion Solutions") are suitable as aqueous electrolyte solutions for the use pursuant to the invention of hemoglobin hyperpolymers. These are known.

Particularly preferred are aqueous electrolyte solutions containing water and sodium chloride in a concentration between 50 and 150 g/L, especially 70 to 100 g/L.

Use

Surprisingly, it is thus possible to improve clinically the severity of acute pulmonary edema, specifically by intravascularly administered chemically modified high molecular weight crosslinked hyperpolymeric hemoglobin as a blood additive, with almost no increase of the volume of the patient's blood. It was not to be expected that such oxygen carriers can be used as an additive in this way when they have the described properties, since these chemically modified high molecular weight crosslinked hemoglobins were and are being actually developed as artificial oxygen carriers and with the objective of supplying peripheral tissue with oxygen. Therefore, their efficacy for improving the therapy of acute pulmonary edema was completely surprising. (Pre)clinical improvement was found in improved survival, or lowered mortality, in an animal model (anesthetized rats) of experimental toxic pulmonary edema, of which the following examples will be given.

The oxygen carrier is administered in such a way that the therapeutic concentrations in the blood plasma, for reasons of increasing viscosity of the blood plasma, are not substantially greater than 50 g/L, for example 50 to 60 g/L, and in particular between 10 and 40 g/L. On the other hand, even very low concentrations (starting at 1 g/L, for example) are sufficient for therapy.

The oxygen carrier can be at concentrations in the aqueous solution of 20 to 200 g/L, especially 50 to 100 g/L.

The agent can be administered as a single dose, or as periodic or irregularly repeated doses, as needed; the method and amount can be adapted to the status, age, sex, and overall condition of the patient.

As far as that goes, therapy of acute pulmonary edema according to the invention is carried out symptomatically and effect-oriented. The frequency of administration of the chemically modified high molecular weight crosslinked hemoglobin, as explained, is between once and an arbitrary maximum value dependent on the outcome. Multiple administration can be according to schedule or controlled by need, regularly or irregularly. The individual dose is governed by the desired therapeutic concentration in the blood plasma and takes into account hemoglobin hyperpolymers already (or still) present in this body compartment, so that a maximum concentration of hemoglobin hyperpolymers in the blood plasma of about 50 to 60 g/L, already unwanted for other reasons, especially the increased viscosity of the blood plasma, is again exceeded only with consideration of the result of an especially cautious and critical risk-benefit analysis for the patient. The initial therapeutic concentration in the blood plasma ($c_m$Hb(PL)) achievable after administration can be estimated from the following equation from the administered dose of hemoglobin hyperpolymer (mHb) and the volume fraction of erythrocytes in the blood (the hematocrit Hkt), and the body weight of the patient (KG):

$$c_m Hb(PL) = mHb \cdot (BV - KG \cdot (1 - Hkt))^{-1}$$

using 60.5 mL/kg (KG) (57 ... 64 mL/kg (KG) as an average value for the blood volume (BV) for women and 69.5 mL/kg (KG) (69 ... 70 mL/kg (KG)) for men.

Preparation of the Agent to be Used Pursuant to the Invention

The agent used is prepared simply by introducing the suitable hemoglobin hyperpolymer(s) into aqueous electrolyte solutions, especially aqueous (sterile) electrolyte solutions that contain the electrolyte(s) in the amount(s) mentioned. The hyperpolymers are molecularly dispersed and can be administered immediately as described, especially by injection.

EXAMPLES

Figure 1:
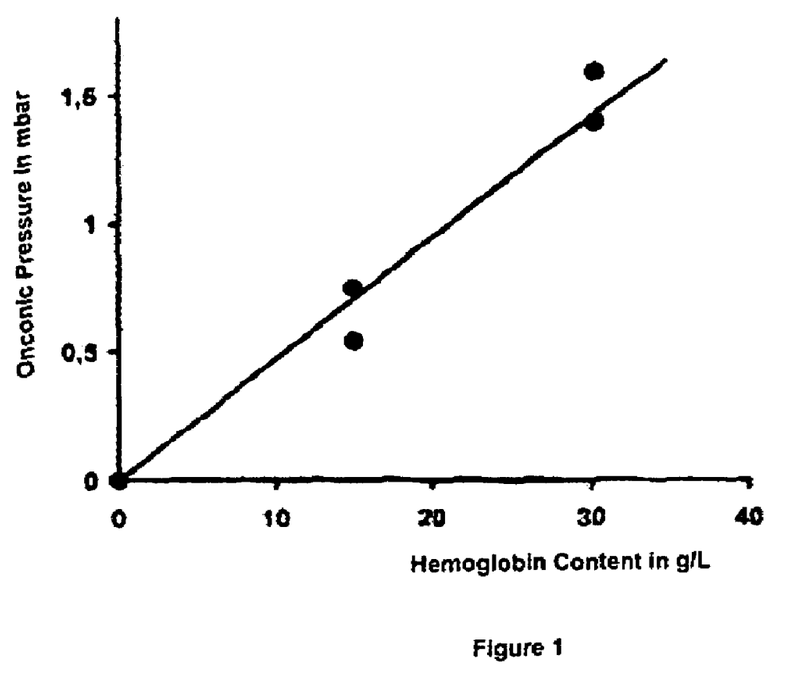
FIG. 1 shows by way of example the dependence of oncotic pressure ($\pi_{onc}$) of a solution of a chemically modified high molecular weight crosslinked hemoglobin pursuant to the invention used for improved treatment of acute pulmonary edema.
Figure 2:
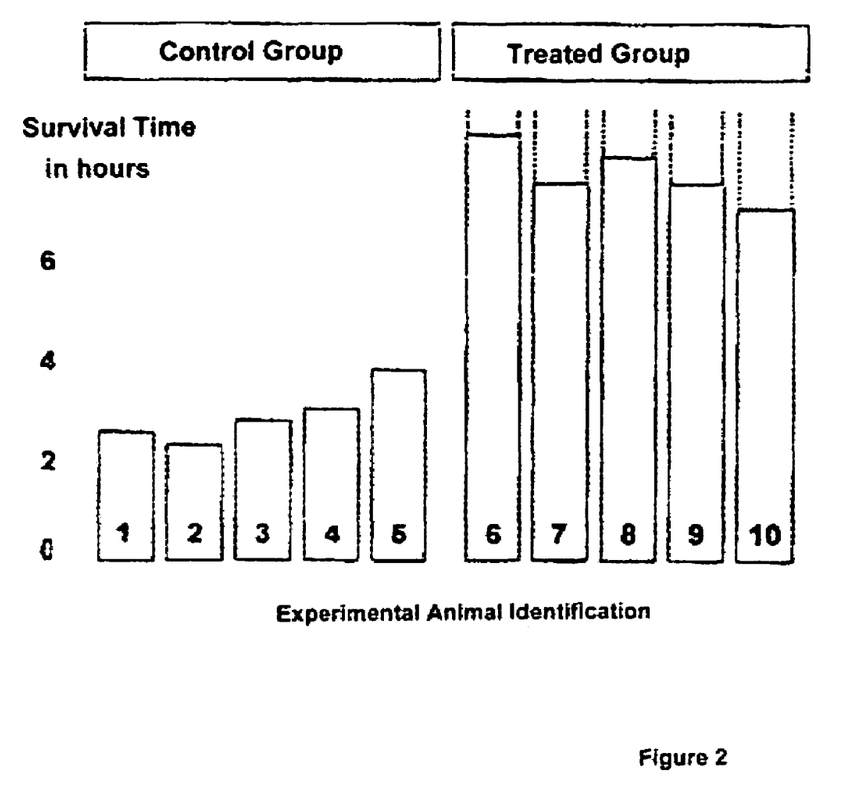
FIG. 2 shows the efficacy of chemically modified high molecular weight crosslinked hemoglobin for improved treatment of acute pulmonary edema, here shown as the survival time of ten anesthetized rats after inducing a lethal toxic pulmonary edema (by injection of oleic acid), five of which were given the drug added to their blood for therapy.

The invention will be explained in further detail with reference to the following examples. FIGS. 1-2 show the following:

FIG. 1 shows by way of example the dependence of the oncotic pressure ($\pi_{onc}$) of a solution of a chemically modified high molecular weight crosslinked hemoglobin (an HP$_3$Hb (pegylated swine hemoglobin hyperpolymer), Batch MR A-A) used pursuant to the invention for the improved treatment of acute pulmonary edema, versus its weight concentration ($c_m$Hb) in an aqueous sodium chloride solution with a concentration of 80 g/L.

FIG. 2 shows the efficacy of chemically modified high molecular weight crosslinked hemoglobin (shown by way of example for an HP$_3$HB, Batch MR A-A) for the improved treatment of acute pulmonary edema, in this case as the survival time of ten anesthetized rats after inducing a lethal toxic pulmonary edema (by injection of oleic acid), of which five animals had the drug added to their blood for treatment.

The following materials were used:

1. The chemically modified high molecular weight crosslinked hemoglobin was a pegylated swine hemoglobin hyperpolymer (an HP$_3$Hb, Batch MR A-A) that was prepared aseptically (on a laboratory scale) principally according to DE (OS) 100 31 740 A 1. Specifically, the batch MR A-A was obtained by preparative ultrafiltration from a mixture of the artificial product batches MR 14, MR 15, and MR 16.

MR 14: Sterile, high-purity swine hemoglobin dissolved at a concentration of 289 g/L in an aqueous electrolyte with the composition 20 mM NaHCO$_3$ and 150 mM NaCl, was deoxygenated at 4° C. by stirring the solution under constantly replaced pure nitrogen, 4 moles of sodium ascorbate per mole of hemoglobin was added (as a 1 molar solution in water) and was allowed to react for about 15 hours, the solution was titrated to a pH of 5.7 with 2 molar lactic acid, 2 moles of inositol hexaphosphate per mole of hemoglobin was added (as a 0.25 molar solution in water), the mixture was titrated after about 1 hour to a pH of 6.5 with 2 molar lactic acid, 9.9 moles of glutaraldehyde per mole of hemoglobin was added (as about a 1.9% solution in deoxygenated water) over a period of 1.5 hours to crosslink the hemoglobin, 1.8 L of water that was equilibrated with nitrogen was added per liter of initial hemoglobin solution, the mixture was titrated after 20 hours to a pH of 6.9 with 0.5 molar sodium hydroxide solution, 20 moles of sodium borohydride per mole of hemoglobin was added (as a 1 molar solution in 0.01 molar sodium hydroxide solution) and was allowed to react for 15 minutes, 4 moles of methoxysuccinimidyl propionate-polyethylene glycol with a molecular weight of 1000 g/mole was added (as an about 25% solution in water) and was allowed to react for 1 hour, and finally the nitrogen atmosphere was replaced by pure oxygen and allowed to equilibrate for 1 hour. Undissolved constituents were separated out by centrifugation (10 min at 20,000 g), and the supernatant solution was filtered for further clarification through filters of decreasing pore size, down to 0.2 μm at the end.

MR 15: Sterile, high-purity swine hemoglobin dissolved at a concentration of 281 g/L in an aqueous electrolyte with the composition 20 mM NaHCO$_3$ and 150 mM NaCl, was deoxygenated at 4° C. by stirring the solution under constantly replaced pure nitrogen, 4 moles of sodium ascorbate per mole of hemoglobin was added (as a 1 molar solution in water) and was allowed to react for about 3 hours, the solution was titrated to a pH of 5.7 with 2 molar lactic acid, 2 moles of inositol hexaphosphate per mole of hemoglobin was added (as a 0.25 molar solution in water), the mixture was titrated after about 1 hour to a pH of 6.3 with 2 molar lactic acid, 9.9 moles of glutaraldehyde per mole of hemoglobin was added (as about a 1.9% solution in deoxygenated water) over a period of 1.5 hours to crosslink the hemoglobin, 1.8 L of water that was equilibrated with nitrogen was added per liter of initial hemoglobin solution, the mixture was titrated after 17 hours to a pH of 6.9 with 0.5 molar sodium hydroxide solution, 20 moles of sodium borohydride per mole of hemoglobin was added (as a 1 molar solution in 0.01 molar sodium hydroxide solution) and was allowed to react for 15 minutes, 4 moles of methoxysuccinimidyl propionate-polyethylene glycol with a molecular weight of 1000 g/mole was added (as an about 25% solution in water) and was allowed to react for 1 hour, and finally the nitrogen atmosphere was replaced by pure oxygen and allowed to equilibrate for 1 hour. Undissolved constituents were separated out by centrifugation (10 min at 20,000 g), and the supernatant solution was filtered for further clarification through filters of decreasing pore size, down to 0.2 μm at the end.

MR 16: Sterile, high-purity swine hemoglobin dissolved at a concentration of 262 g/L in an aqueous electrolyte with the composition 20 mM NaHCO$_3$ and 150 mM NaCl, was deoxygenated at 4° C. by stirring the solution under constantly replaced pure nitrogen, 4 moles of sodium ascorbate per mole of hemoglobin was added (as a 1 molar solution in water) and was allowed to react for about 27 hours, the solution was titrated to a pH of 5.8 with 2 molar lactic acid, 2 moles of inositol hexaphosphate per mole of hemoglobin was added (as a 0.25 molar solution in water), the mixture was titrated after about 1.5 hours to a pH of 6.5 with 2 molar lactic acid, 9.9 moles of glutaraldehyde per mole of hemoglobin was added (as about a 1.9% solution in deoxygenated water) over a period of 1.5 hours to crosslink the hemoglobin, 1.8 L of water that was equilibrated with nitrogen was added per liter of initial hemoglobin solution, the mixture was titrated after 17 hours to a pH of 6.9 with 0.5 molar sodium hydroxide solution, 20 moles of sodium borohydride per mole of hemoglobin was added (as a 1 molar solution in 0.01 molar sodium hydroxide solution) and was allowed to react for 1.5 hours, 4 moles of methoxysuccinimidyl propionate-polyethylene glycol with a molecular weight of 1000 g/mole was added (as an about 25% solution in water) and was allowed to react for 1 hour, and finally the nitrogen atmosphere was replaced by pure oxygen and allowed to equilibrate for 1 hour. Undissolved constituents were separated out by centrifugation (10 min at 20,000 g), and the supernatant solution was filtered for further clarification through filters of decreasing pore size, down to 0.2 µm at the end.

MR A-A: 3720 mL of MR 14 with 107 g of hemoglobin polymer, 3600 mL of MR 15 with 115 g of hemoglobin polymer, and 3900 mL of MR 16 with 127 g of hemoglobin polymer were mixed and fractionated in several portions in an ultrafiltration system (Centramate from Pall-Filtron) at an average concentration of 40 g/L, over and through cellulose acetate membranes with a nominal molecular weight exclusion limit of 1 MDa, with the filtrate flow rate having been adjusted by a valve to values below 50% of the maximum (the so-called water flow rate), and each time using at least ten times the sample volume of diafiltration solution (this contained sodium chloride at a concentration of 80 g/L) in a continuous diafiltration mode for simultaneous solvent exchange. At the end, the retentates were concentrated and later combined.

This preparatively separated fraction of the drug had a molecular weight distribution with a number average molecular weight of 230,000 g/mole and a medial molecular weight of 993,000 g/mole. The drug thus obtained was used in a sterile aqueous solution, sufficiently low in endotoxin according to Ph. Eur., of 80 g/L NaCl in WFI (water for injection). Its content by weight was 58 g/L, and the pH of the preparation was 7.3.

2. The experimental animals were white laboratory rats with an average weight of about 350 g (the range of body weights of all of the ten animals used was between 315 and 390 g), that were bred and maintained according to applicable animal protection laws. Until the day prior to the particular experiment, they had free access to sufficient food; they could drink until just before beginning the experiment.

The following special methods of determination were used:

1. Hemoglobin contents were measured photometrically using the Drabkin cyanohemoglobin method ('Hemoglobin color test MRP3', Boehringer Mannheim, Germany); pH values were measured potentiometrically (glass pH electrode) with a blood gas analyzer ('ABL 5', Radiometer, Willich, Germany).

2. The molecular weight distributions of the crosslinked hemoglobins and their characteristic parameters were determined by volume exclusion chromatography (Pötzschke H. et al. (1997): "Molar Masses and Structure in Solution of Haemoglobin Hyperpolymers—A Common Calibration of Size Exclusion Chromatography of These Artificial Oxygen Carriers," Artificial Cells, Blood Substitutes, and Immobilization Biotechnology 25, 527-540) on Sephacryl S-400 HR gel (Pharmacia Biotech, Freiburg, Germany).

3. The oncotic pressures of aqueous solutions of the crosslinked hemobglobins were determined with membrane osmometers (membrane osmometer or colloid osmometer, Knauer, Berlin, Germany) using an aqueous saline solution (80 g/L NaCl and 0.2 g/L $NaN_3$) as solvent and cellulose acetate membranes with a nominal molecular weight exclusion limit of 20,000 Da.

Example of Embodiment 1

Control Group

Five laboratory rats were given systemic complete anesthesia by intraperitoneal injection of 50 mg pentobarbital per kg of body weight. The depth of anesthesia was kept constant over time in the (surgically) tolerant state (the 3rd classical state of narcosis according to A. Guedel), by administering after each occurrence of an active pain reaction (retraction) to periodic pinching of a paw an additional 17 mg of pentobarbital per kg of body weight as a maintenance dose (about every 90 min). The animals were given a venous catheter of PE tubing implanted in a jugular vein, and in the further course of the experiment, about 0.5 mL of an isotonic saline solution (90 g of NaCl per L of solution) was administered through this catheter intravenously each hour to maintain a compensated fluid balance.

To produce acute toxic pulmonary edema, 46 µL of oleic acid per kg of body weight was administered uniformly to the animals intravenously over a period of three minutes.

FIG. 2 in the left section shows the survival times of the five animals, all of which died in less than four hours, four of them even in less than three hours (calculated from the time of injection of the oleic acid).

Example of Embodiment 2

Treated Group

Five other rats were treated as in Example of Embodiment 1 in exactly the same way with the single exception that 2.5 mL of the preparation of chemically modified high molecular weight crosslinked hemoglobin (an $HP_3Hb$, a pegylated swine hemoglobin hyperpolymer—Batch MR A-A) was administered to each of them intravenously 15 and 45 minutes after the intravenous administration of oleic acid. The average hemoglobin content of the blood plasma after the second administration was about 23 g/L, which then was slowly reduced (with a plasma half-life of about 18 hours).

FIG. 2 in the right section shows these five animals, who without exception survived longer than seven hours and ultimately were sacrificed under anesthesia to end the experiment. Comparison of the survival times of the animals in the two experimental groups shows the enormous efficacy of the hemoglobin hyperpolymers for preventing the spontaneous lethality of toxic pulmonary edema induced here experimentally.

The invention claimed is:

1. A method of treating acute pulmonary edema comprising:
   (a) providing an aqueous hypo-oncotic solution comprising electrolytes and high molecular weight intermolecularly crosslinked hyperpolymeric hemoglobin, which is further chemically modified by at least one of covalent linkage to chemically reactive effectors of oxygen binding, and covalent linkage to other macromolecules selected from the group consisting of poly(ethylene oxides), poly(ethylene glycols), dextranes, and hydroxyethylstarches; and
   (b) administering the solution to a person to treat acute pulmonary edema, wherein the solution before administration to a person has a (hypo) oncotic pressure below 5 mbar.

2. The method pursuant to claim 1, wherein the chemically modified hyperpolymeric hemoglobin originates from humans, swine, or cattle.

3. The method pursuant to claim 1, wherein the solution contains sodium chloride at a concentration between 50 and 150 g/L.

4. The method pursuant to claim 1, wherein the electrolytes are selected to correspond with physiological ambient media in the person the solution is intended to be administered to.

5. The method pursuant to claim 1, further comprising covalently bonding a polyalkylene oxide to the modified hyperpolymeric hemoglobin prior to administering the solution to a person.

6. The method pursuant to claim 1, wherein the solution is administered to the person by intravascular injection.

7. The method pursuant to claim 1, wherein the solution is administered to the person at least twice.

* * * * *

UNITED STATES PATENT AND TRADEMARK OFFICE
CERTIFICATE OF CORRECTION

PATENT NO.      : 7,598,220 B2                                          Page 1 of 1
APPLICATION NO. : 10/578428
DATED           : October 6, 2009
INVENTOR(S)     : Wolfgang Barnikol It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 452 days.

Signed and Sealed this

Twenty-eighth Day of September, 2010

David J. Kappos
*Director of the United States Patent and Trademark Office*